United States Patent
Aguilar et al.

(10) Patent No.: US 12,247,965 B1
(45) Date of Patent: Mar. 11, 2025

(54) AIR QUALITY NOTIFICATION SYSTEM

(71) Applicant: Samsara Inc., San Francisco, CA (US)

(72) Inventors: Ernie Aguilar, Austin, TX (US); Christian Almer, San Francisco, CA (US); David Gal, Oakland, CA (US); Mintu Abraham, San Mateo, CA (US); Somasundara Pandian, San Francisco, CA (US); Gautam Ramaswamy, San Francisco, CA (US); Zoe Demertzis, San Jose, CA (US)

(73) Assignee: Samsara Inc., San Francisco, CA (US)

( * ) Notice: Subject to any disclaimer, the term of this patent is extended or adjusted under 35 U.S.C. 154(b) by 272 days.

(21) Appl. No.: 17/660,316

(22) Filed: Apr. 22, 2022

(51) Int. Cl.
*G01N 33/00* (2006.01)
*H04L 67/12* (2022.01)

(52) U.S. Cl.
CPC ..... *G01N 33/0063* (2013.01); *G01N 33/0075* (2013.01); *H04L 67/12* (2013.01)

(58) Field of Classification Search
None
See application file for complete search history.

(56) References Cited

U.S. PATENT DOCUMENTS

| | | | | |
|---|---|---|---|---|
| 5,132,968 A | * | 7/1992 | Cephus | G08B 26/007 370/349 |
| 5,406,265 A | * | 4/1995 | Trozzo | G08B 1/08 340/693.5 |
| 6,114,964 A | * | 9/2000 | Fasano | G01N 33/0075 340/628 |
| 6,670,887 B2 | * | 12/2003 | Dungan | G08B 21/16 340/632 |
| 8,190,367 B2 | * | 5/2012 | Bassa | F24F 11/30 73/31.03 |
| 8,717,161 B1 | * | 5/2014 | Gary | G08B 25/08 340/539.22 |
| 2002/0070869 A1 | * | 6/2002 | Dungan | G01N 33/0073 340/506 |
| 2014/0238107 A1 | * | 8/2014 | Chou | G01N 33/0075 73/23.36 |
| 2016/0266081 A1 | * | 9/2016 | Risk | G01N 21/3504 |
| 2023/0298452 A1 | * | 9/2023 | Miller | G08B 21/0492 701/423 |

FOREIGN PATENT DOCUMENTS

| | | | | |
|---|---|---|---|---|
| CN | 105874520 B | * | 11/2018 | F24F 11/30 |
| KR | 20120007983 A | * | 1/2012 | G01N 33/222 |

* cited by examiner

*Primary Examiner* — Daniel S Larkin
(74) *Attorney, Agent, or Firm* — Schwegman Lundberg & Woessner, P.A.

(57) ABSTRACT

An air quality notification system to perform operations that include: causing a sensor device to sample an air quality associated with a location at a predefined sampling interval; determining, at the sensor device, that a value corresponding with the air quality sampled by the sensor device transgresses a threshold value; causing the sensor device to transmit an alert to a server system responsive to the determining that the value corresponding with the air quality transgresses a threshold value; and causing the server system to present a notification at a client device responsive to the sensor device transmitting the alert, the notification including at least a display of an identifier associated with the location.

20 Claims, 7 Drawing Sheets

300 

```
┌─────────────────────────────────────────────────────────────┐
│  CAUSING A SENSOR DEVICE TO SAMPLE AN AIR QUALITY ASSOCIATED│
│    WITH A LOCATION AT A PREDEFINED SAMPLING INTERVAL        │
│                          302                                │
└─────────────────────────────────────────────────────────────┘
                              │
                              ▼
┌─────────────────────────────────────────────────────────────┐
│ DETERMINING, AT THE SENSOR DEVICE, THAT A VALUE CORRESPONDING│
│   WITH THE AIR QUALITY SAMPLED BY THE SENSOR DEVICE         │
│            TRANSGRESSES A THRESHOLD VALUE                   │
│                          304                                │
└─────────────────────────────────────────────────────────────┘
                              │
                              ▼
┌─────────────────────────────────────────────────────────────┐
│  CAUSING THE SENSOR DEVICE TO TRANSMIT AN ALERT TO A SERVER │
│   SYSTEM RESPONSIVE TO THE DETERMINING THAT THE VALUE       │
│ CORRESPONDING WITH THE AIR QUALITY TRANSGRESSES A THRESHOLD │
│                         VALUE                               │
│                          306                                │
└─────────────────────────────────────────────────────────────┘
                              │
                              ▼
┌─────────────────────────────────────────────────────────────┐
│   CAUSING THE SERVER SYSTEM TO PRESENT A NOTIFICATION AT A  │
│  CLIENT DEVICE RESPONSIVE TO THE SENSOR DEVICE TRANSMITTING │
│   THE ALERT, THE NOTIFICATION INCLUDING AT LEAST A DISPLAY OF AN │
│      IDENTIFIER ASSOCIATED WITH THE SENSOR DEVICE           │
│                          308                                │
└─────────────────────────────────────────────────────────────┘
```

*FIG. 3*

AIR QUALITY NOTIFICATION SYSTEM

TECHNICAL FIELD

Embodiments of the present disclosure relate generally to the field of air quality monitoring, and more specifically to remotely monitoring air quality.

BACKGROUND

Air quality is typically in the context of indoor or outdoor pollutants such as smog, car exhaust, or smoke. The negative effects of poor outdoor air quality has on an individual's health has been well studied and is commonly known. Air quality sensors are devices that monitor the presence of air pollution in the surrounding area. They can be used for both indoor and outdoor environments. There are various types of air pollution sensors that may detect a number of different components. For example, these components may include: ozone, particulate matter, carbon monoxide, sulfur dioxide, and nitrous oxide. These sensors can help serve many purposes and help bring attention to environmental issues beyond the scope of the human eye.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 3 is a flowchart depicting a method of causing display of a notification at a client device, according to certain example embodiments.

DETAILED DESCRIPTION

Figure 1:
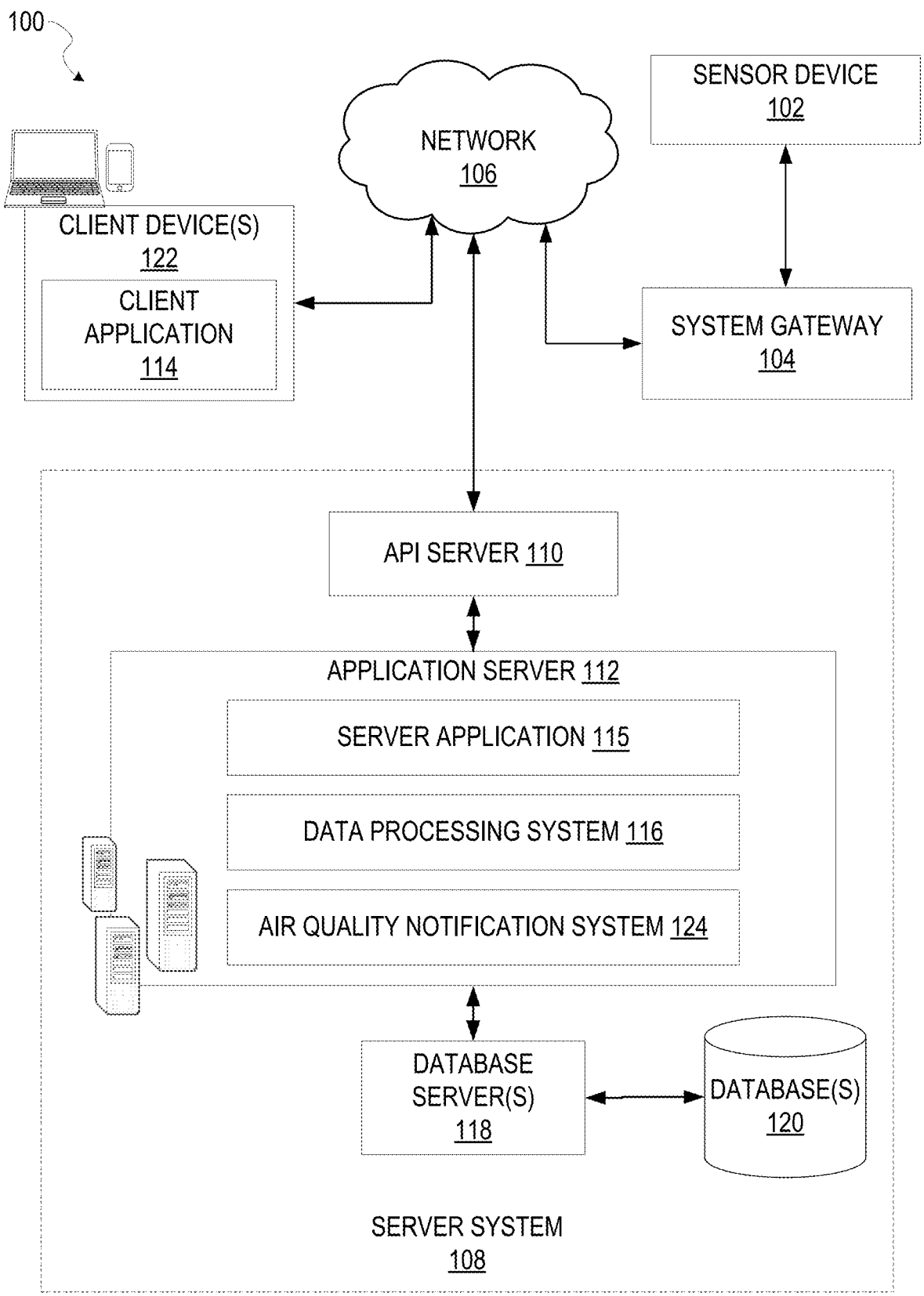
FIG. 1 is a block diagram showing an example system for exchanging data (e.g., sensor data and associated content) over a network in accordance with some embodiments, wherein the system includes an air quality sensor system.

As discussed above, air quality sensors are devices that monitor the presence of air pollution in the surrounding area, and can be used for both indoor and outdoor environments. Although the existing systems provide users' with general information related to the air quality is an area, they do not provide a significant amount of meaningful information related to the air quality, let alone provide real-time notification of air quality in a given area. Accordingly, a system for detecting and providing notifications related to dangerous air quality conditions in real-time is described herein.

According to certain example embodiments, an air quality notification system is configured to perform operations that include: causing a sensor device to sample an air quality associated with a location at a predefined sampling interval; determining, at the sensor device, that a value corresponding with the air quality sampled by the sensor device transgresses a threshold value; causing the sensor device to transmit an alert to a server system responsive to the determining that the value corresponding with the air quality transgresses a threshold value; and causing the server system to present a notification at a client device responsive to the sensor device transmitting the alert, the notification including at least a display of an identifier associated with the location.

In some example embodiments, the sensor device may be configured to sample the air quality in a given area at a first sampling rate, and upon determining that a value of an air quality sample transgresses a threshold value, may begin sampling the air quality at a second sampling rate, wherein the second sampling rate is higher (i.e., more frequent) that the first sampling rate. For example, the sensor device may sample the air quality in a given area at a rate of one sample a minute, wherein the sample of the air quality comprises a value that may indicate a size of particulate matter, or a parts-per-million amount of the particulate in the air.

The air quality notification system may determine that the value of the air quality transgresses a threshold value. For example, the size of the particulate matter may be below a threshold diameter, or the parts-per-million amount of the particulate may be greater than a threshold value. Upon determining that the value of the air quality sample transgresses the threshold value, the air quality notification system may cause the sensor device to sample the air quality at a second sampling rate, wherein the second sampling rate is greater than the first sampling rate.

In some embodiments, the sensor device may include a first sensor device among a plurality of sensor devices. Responsive to determining that a value of an air quality sample from the first sensor device transgresses a threshold value, the air quality notification system may activate a second sensor device. For example, the second sensor device may be configured to sample the air quality of a location proximate to the area sampled by the first sensor device.

In some embodiments, the notification presented by the air quality notification system may include a display of an icon at a position within a map image that depicts a location monitored by the sensor device. For example, the map image may comprise a display of one or more icons that represent sensor devices which may be located at positions within the location depicted by the map image. In some embodiments, the icons may be labeled with an identifier that corresponds with the sensor device.

In some embodiments, a user may provide an input to select an icon presented within the map image, and in response, the air quality notification system may present a menu element to display attributes associated with the sensor device, and data generated by the sensor device.

FIG. 1 is a block diagram showing an example system 100 for sampling air quality, according to certain example embodiments. The system 100 includes one or more client devices 122 that host a number of applications including a client application 114.

Accordingly, each client application 114 is able to communicate and exchange data with another client application 114 and with the server application 115 executed at the server system 108 via the network 106. The data exchanged between client applications 114, and between a client application 114 and the server system 108, includes functions (e.g., commands to invoke functions) as well as payload data (e.g., text, audio, video or other multimedia data).

The server system 108 provides server-side functionality via the network 106 to a particular client application 114, and in some embodiments to the sensor device 102 and the system gateway 104. While certain functions of the system 100 are described herein as being performed by either a client application 114, the sensor device 102, the system gateway 104, or by the server system 108, it will be appreciated that the location of certain functionality either within the client application 114 or the server system 108 is a design choice. For example, it may be technically preferable to initially deploy certain technology and functionality within the server system 108, but to later migrate this technology and functionality to the client application 114, or one or more processors of the sensor device 102, or system gateway 104, where there may be sufficient processing capacity.

The server system 108 supports various services and operations that are provided to the client application 114. Such operations include transmitting data to, receiving data from, and processing data generated by the client application 114, the sensor device 102, and the system gateway 104. In some embodiments, the sensor device 102 may include an odometer associated with a vehicle, as well as a GPS associated with the vehicle. In some embodiments, this data includes, message content, device information, geolocation information, persistence conditions, social network information, sensor data, and live event information, as examples. In other embodiments, other data is used. Data exchanges within the system 100 are invoked and controlled through functions available via graphical user interfaces (GUIs) of the client application 114.

Turning now specifically to the server system 108, an Application Program Interface (API) server 110 is coupled to, and provides a programmatic interface to, an application server 112. The application server 112 is communicatively coupled to a database server 118, which facilitates access to a database 120 that stores data associated with data generated by the sensor device 102 and processed by the application server 112.

Dealing specifically with the API server 110, this server receives and transmits data (e.g., sensor data, commands, and payloads) between the client device 122 and the application server 112. Specifically, the API server 110 provides a set of interfaces (e.g., routines and protocols) that can be called or queried by the client application 114 in order to invoke functionality of the application server 112. The API server 110 exposes various functions supported by the application server 112, including account registration, login functionality, the transmission of data, via the application server 112, from a particular client application 114 to another client application 114, the sending of sensor data (e.g., images, video, geolocation data, inertial data, temperature data, etc.) from a client application 114 to the server application 115, and for possible access by another client application 114, the setting of a collection of data, the retrieval of such collections, the retrieval of data, and the location of devices within a region.

The application server 112 hosts a number of applications and subsystems, including a server application 115, and an air quality notification system 124. According to certain example embodiments, the air quality notification system 124 is configured to perform operations that include: causing a sensor device to sample an air quality associated with a location at a predefined sampling interval; determining, at the sensor device, that a value corresponding with the air quality sampled by the sensor device transgresses a threshold value; causing the sensor device to transmit an alert to a server system responsive to the determining that the value corresponding with the air quality transgresses a threshold value; and causing the server system to present a notification at a client device responsive to the sensor device transmitting the alert, the notification including at least a display of an identifier associated with the location. Further details of the air quality notification system 124 can be found in FIG. 2 below.

The server application 115 implements a number of data processing technologies and functions, particularly related to the aggregation and other processing of data (e.g., sensor data generated by the sensor device 102). As will be described in further detail, the sensor data, including temporal data, asset status data, and GPS data points, generated by the sensor device 102 may be aggregated into collections associated with a particular user account. Other processor and memory intensive processing of data may also be performed server-side by the server application 115, in view of the hardware requirements for such processing.

The application server 112 is communicatively coupled to a database server 118, which facilitates access to a database 120 in which is stored data associated with sensor data generated by the sensor device 102 and processed by the server application 115.

Figure 2:
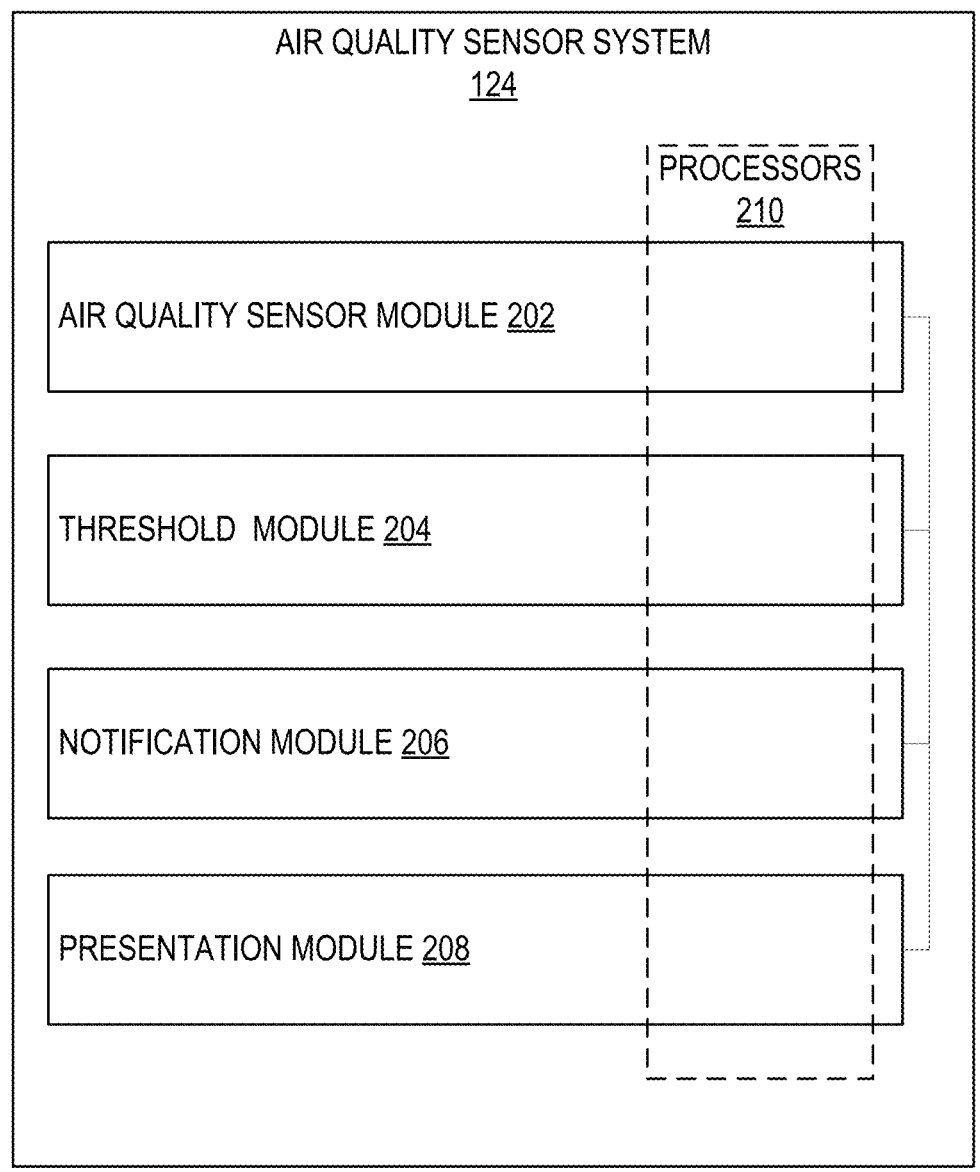
FIG. 2 is a block diagram illustrating various modules of an air quality sensor system, according to certain example embodiments.

FIG. 2 is a block diagram 200 illustrating components of the air quality notification system 124 that configure the air quality notification system 124 to perform operations to present notifications based on detected air quality conditions, according to some example embodiments.

The air quality notification system 124 is shown as including an air quality sensor module 202, a threshold module 204, a notification module 206, and a presentation module 208, all configured to communicate with each other (e.g., via a bus, shared memory, or a switch). Any one or more of these modules may be implemented using one or more processors 210 (e.g., by configuring such one or more processors to perform functions described for that module) and hence may include one or more of the processors 210.

Any one or more of the modules described may be implemented using hardware alone (e.g., one or more of the processors 210 of a machine) or a combination of hardware and software. For example, any module described of the air quality notification system 124 may physically include an arrangement of one or more of the processors 210 (e.g., a subset of or among the one or more processors of the machine) configured to perform the operations described herein for that module. As another example, any module of the air quality notification system 124 may include software, hardware, or both, that configure an arrangement of one or more processors 210 (e.g., among the one or more processors of the machine) to perform the operations described herein for that module. Accordingly, different modules of the air quality notification system 124 may include and configure different arrangements of such processors 210 or a single arrangement of such processors 210 at different points in time. Moreover, any two or more modules of the air quality notification system 124 may be combined into a single module, and the functions described herein for a single module may be subdivided among multiple modules. Furthermore, according to various example embodiments, modules described herein as being implemented within a single machine, database, or device may be distributed across multiple machines, databases, or devices.

FIG. 3 is a flowchart depicting a method 300 of causing display of a notification at a client device 102, according to certain example embodiments. Operations of the method 300 may be performed by the modules described above with respect to FIG. 2. As shown in FIG. 3, the method 300 includes one or more operations 302, 304, 306, and 308.

At operation 302, the air quality sensor module 202 causes a sensor device 102 to generate an air quality sample of an air quality associated with a location at a predefined sampling interval. For example, the sensor device 102 may be configured to sample the air quality at a location once every minute.

At operation 304, the threshold module 304 determines that a value corresponding with an air quality sample sampled by the sensor device 102 transgresses a threshold value. The threshold value may be defined by an administrator of the air quality notification system 124, and assigned to one or more locations, or one or more sensor devices 102. In some embodiments, the threshold may indicate a maximum parts-per-millions amount of airborne particulate, as well as a minimum particulate diameter.

At operation 306, the air quality sensor module 202 causes the sensor device 102 to transmit an alert to a server system responsive to the threshold module 204 determining that the value corresponding with the air quality sample transgresses the threshold value. For example, the alert may comprise attributes of the sensor device 102 (i.e., a sensor identifier, a location identifier), as well as an indication of the value of the air quality sample.

In some embodiments, responsive to the threshold module 204 determining that the air quality sample generated by the sensor device 102 transgresses the threshold value, the air quality sensor module 202 may cause the sensor device 102 to change or adjust the sampling rate. For example, the sensor device 102 may sample the air quality at a first sampling rate, and upon determining that a value corresponding to the air quality sample transgresses the threshold value, the air quality sensor module 202 may cause the sensor device 102 to sample the air quality at a second sampling rate, wherein the second sampling rate is higher than the first sampling rate.

At operation 308, the notification module 206 causes the server system to transmit a notification to a client device 122 responsive to the senor device 102 transmitting the alert. The presentation module 208 may cause the client device 122 to cause display of the notification, wherein the notification comprises a display of an identifier associated with the sensor device and an indication of the location, as well as an indication of the value of the air quality sample.

Figure 4:
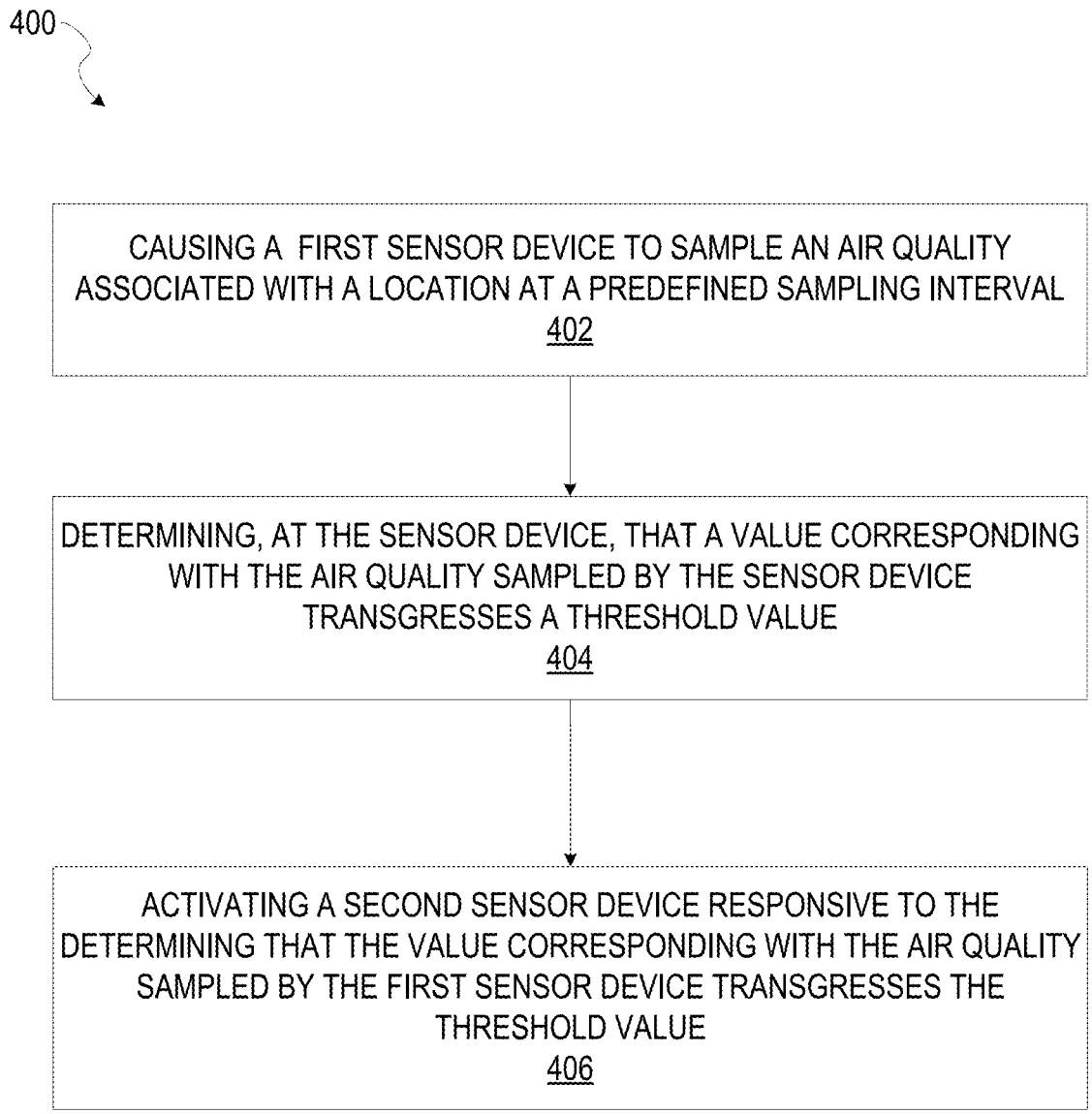
FIG. 4 is a flowchart depicting a method of activating a sensor device, according to certain example embodiments.

FIG. 4 is a flowchart depicting a method 400 of activating a sensor device 102, according to certain example embodiments. Operations of the method 400 may be performed by the modules described above with respect to FIG. 2. In some embodiments, the method 400 may be performed as a subroutine of one or more operations of the method 300, such as operation 308. As shown in FIG. 4, the method 400 includes one or more operations 402, 404, and 406.

In some embodiments, the sensor device 102 may be a first sensor device among a plurality of sensor devices configured to monitor air quality within a location. Accordingly, at operation 402, the air quality sensor module 202 causes the first sensor device to sample an air quality associated with a location at a predefined sampling interval.

At operation 404, as in operation 304, the threshold module 304 determines that a value corresponding with an air quality sample sampled by the first sensor device transgresses a threshold value. As discussed above, the threshold value may be defined by an administrator of the air quality notification system 124, and assigned to a location, or one or more sensor devices 102. For example, a first threshold may be assigned to the first sensor device, while a second threshold may be assigned to a second sensor device.

At operation 406, responsive to the threshold module 304 determining that the value corresponding with the air quality sample sampled by the first sensor device transgresses the threshold value, the air quality sensor module 202 activates a second sensor device, wherein the second sensor device may be at a location proximate to the first sensor device.

Figure 5:
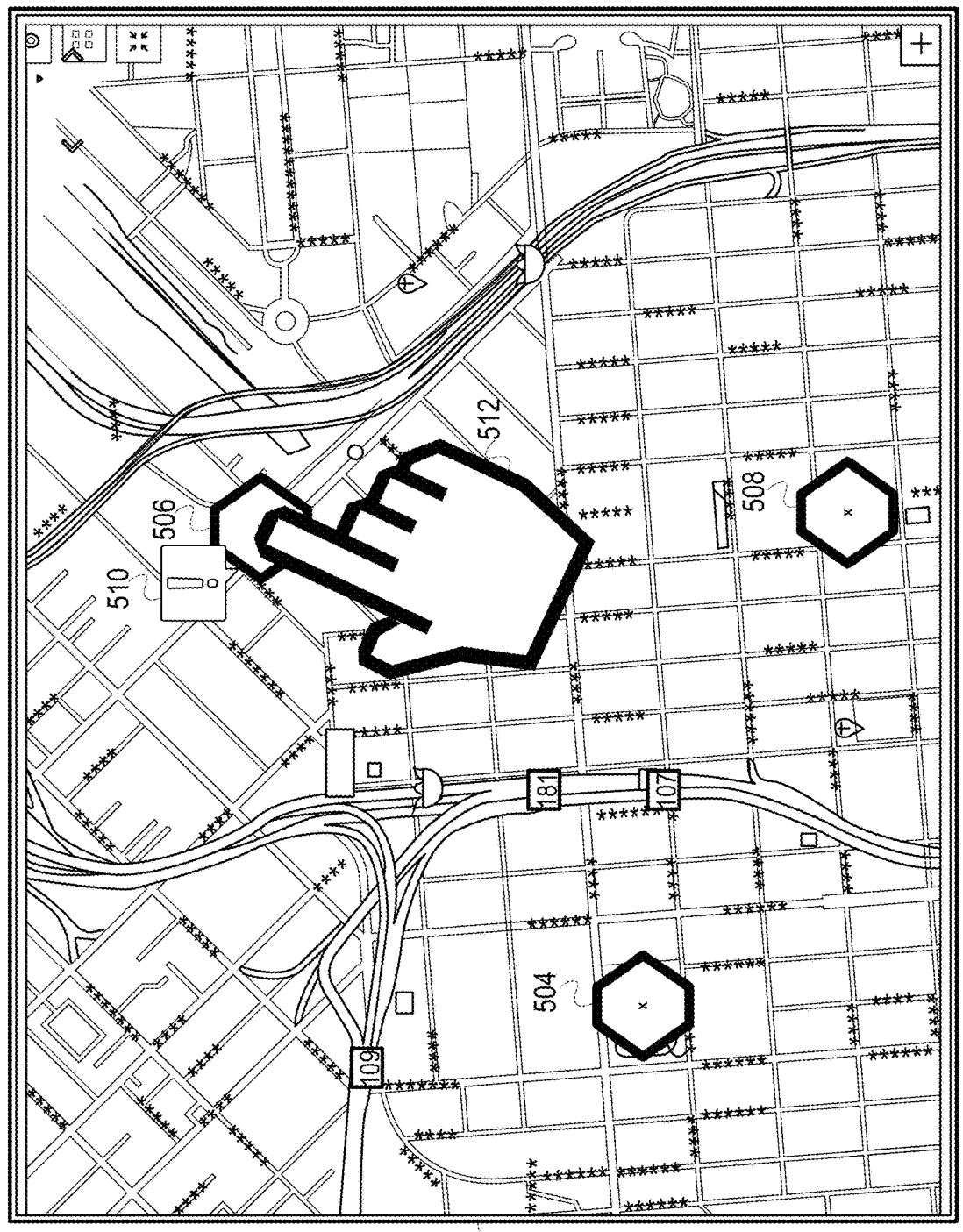
FIG. 5 is an interface diagram illustrating a graphical user interface (GUI) presented by an air quality notification system, according to certain example embodiments.

FIG. 5 is an interface diagram 500 illustrating a GUI 502 presented by an air quality notification system 124 at a client device 122, according to certain example embodiments. As seen in the interface diagram 500, the GUI 502 may comprise a map image that displays one or more icons 504, 506, and 508 that indicate locations of sensor devices 102 (i.e., air quality sensors) within the location depicted by the map image.

In some embodiments, the icons 504, 506, and 508 may comprise a display of an identifier associated with a corresponding sensor device 102. For example, the icons 504, 506, and 508 may include a display of an identifier that identifies a sensor device 102.

In some embodiments, responsive to a sensor device 102 determining that a value of an air quality sample transgresses a threshold value, as discussed in the methods 300 and 400 above, the air quality notification system 124 may present an alert 510, wherein the alert 510 may provide an indication of which sensor device 102 among a plurality of sensor devices 102 has determined that an air quality value has transgressed a threshold value.

In some embodiments, a user of the client device 122 may provide an input 512 that selects an icon 506 in order to access and display additional detail related to the corresponding sensor device 102. For example, the interface diagram 600 depicted in FIG. 6 provides an illustrative example of a GUI 602 to display further information related to a sensor device 102.

Figure 6:
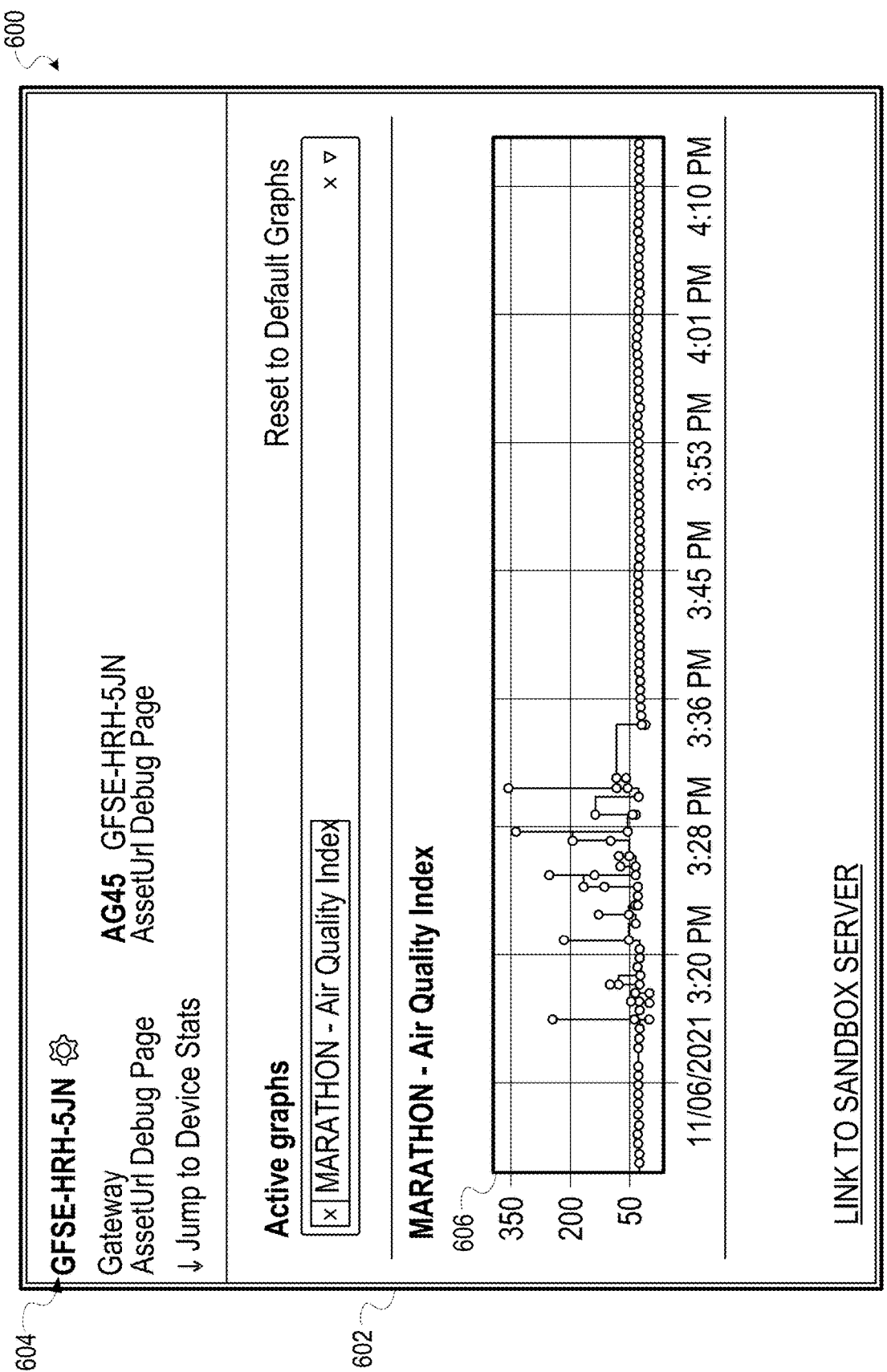
FIG. 6 is an interface diagram illustrating a GUI presented by an air quality notification system, according to certain example embodiments.

FIG. 6 is an interface diagram 600 illustrating a GUI 602 presented by an air quality notification system 124 at a client device 122, according to certain example embodiments. As seen in the interface diagram 600, the GUI 602 may comprise a display of an identifier 604 associated with a sensor device 102, and a display of a graph element 606 to display air quality samples generated by the sensor device 102 over time.

In some embodiments, the GUI 602 may be presented responsive to receiving a request from a client device 122, wherein the request includes an identification of a sensor device 102. For example, a user of the client device 122 may provide an input to select an icon that corresponds with a sensor device 102, such as the icon 506 presented within the GUI 502.

Figure 7:
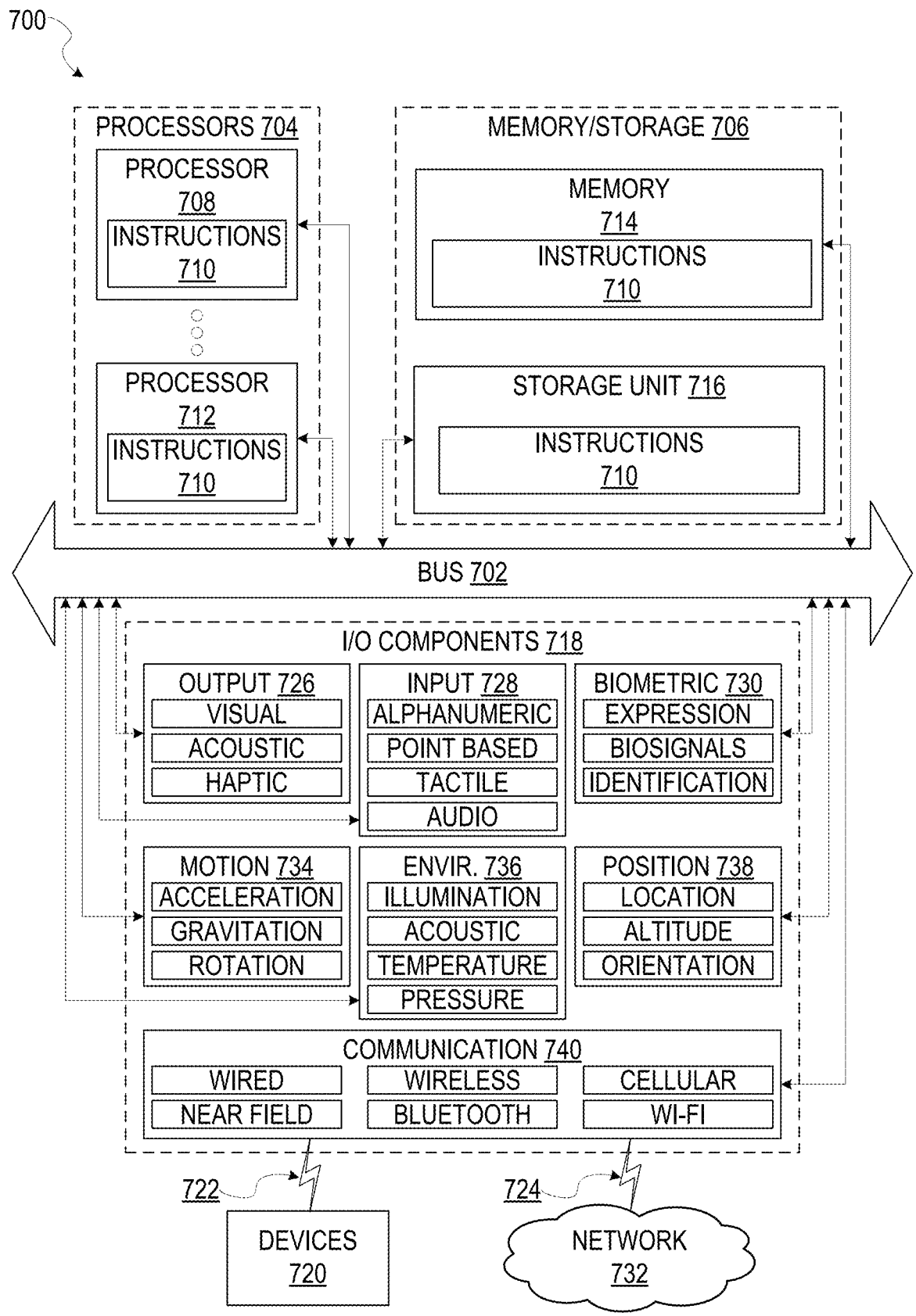
FIG. 7 is a block diagram illustrating components of a machine, according to some example embodiments, able to read instructions from a machine-readable medium (e.g., a machine-readable storage medium) and perform any one or more of the methodologies discussed herein.

FIG. 7 is a block diagram illustrating components of a machine 700, according to some example embodiments, able to read instructions from a machine-readable medium (e.g., a machine-readable storage medium) and perform any one or more of the methodologies discussed herein. Specifically, FIG. 7 shows a diagrammatic representation of the machine 700 in the example form of a computer system, within which instructions 710 (e.g., software, a program, an application, an applet, an app, or other executable code) for causing the machine 700 to perform any one or more of the methodologies discussed herein may be executed. As such, the instructions 710 may be used to implement modules or components described herein. The instructions 710 transform the general, non-programmed machine 700 into a particular machine 700 programmed to carry out the described and illustrated functions in the manner described. In alternative embodiments, the machine 700 operates as a standalone device or may be coupled (e.g., networked) to other machines. In a networked deployment, the machine 700 may operate in the capacity of a server machine or a client machine in a server-client network environment, or as a peer machine in a peer-to-peer (or distributed) network environment. The machine 700 may comprise, but not be limited to, a server computer, a client computer, a personal computer (PC), a tablet computer, a laptop computer, a netbook, a personal digital assistant (PDA), an entertainment media system, a cellular telephone, a smart phone, a mobile device, a wearable device (e.g., a smart watch), other smart devices, a web appliance, a network router, a network switch, a network bridge, or any machine capable of executing the instructions 710, sequentially or otherwise, that specify actions to be taken by machine 700. Further, while only a single machine 700 is illustrated, the term "machine" shall also be taken to include a collection of machines that individually or jointly execute the instructions 710 to perform any one or more of the methodologies discussed herein.

The machine 700 may include processors 704 (i.e., processor 708 through processor 712), memory memory/storage 706, and I/O components 718, which may be configured to communicate with each other such as via a bus 702. The memory/storage 706 may include a memory 714, such as a main memory, or other memory storage, and a storage unit 716, both accessible to the processors 704 such as via the bus 702. The storage unit 716 and memory 714 store the instructions 710 embodying any one or more of the methodologies or functions described herein. The instructions 710 may also reside, completely or partially, within the memory 714, within the storage unit 716, within at least one of the processors 704 (e.g., within the processor's cache memory), or any suitable combination thereof, during execution thereof by the machine 700. Accordingly, the memory 714, the storage unit 716, and the memory of processors 704 are examples of machine-readable media.

The I/O components 718 may include a wide variety of components to receive input, provide output, produce output, transmit information, exchange information, capture measurements, and so on. The specific I/O components 718 that are included in a particular machine 700 will depend on the type of machine. For example, portable machines such as mobile phones will likely include a touch input device or other such input mechanisms, while a headless server machine will likely not include such a touch input device. It will be appreciated that the I/O components 718 may include many other components that are not shown in FIG. 7. The I/O components 718 are grouped according to functionality merely for simplifying the following discussion and the grouping is in no way limiting. In various example embodiments, the I/O components 718 may include output components 726 and input components 728. The output components 726 may include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 728 may include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 718 may include biometric components 730, motion components 734, environmental environment components 736, or position components 738 among a wide array of other components. For example, the biometric components 730 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram based identification), and the like. The motion components 734 may include acceleration sensor components (e.g., accelerometer), gravitation sensor components, rotation sensor components (e.g., gyroscope), and so forth. The environment components 736 may include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that may provide indications, measurements, or signals corresponding to a surrounding physical environment. The position components 738 may include location sensor components (e.g., a Global Position system (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 718 may include communication components 740 operable to couple the machine 700 to a network 732 or devices 720 via coupling 722 and coupling 724 respectively. For example, the communication components 740 may include a network interface component or other suitable device to interface with the network 732. In further examples, communication components 740 may include wired communication components, wireless communication components, cellular communication components, Near Field Communication (NFC) components, Bluetooth® components (e.g., Bluetooth® Low Energy), Wi-Fi® components, and other communication components to provide communication via other modalities. The devices 720 may be another machine or any of a wide variety of peripheral devices (e.g., a peripheral device coupled via a Universal Serial Bus (USB)).

Moreover, the communication components 740 may detect identifiers or include components operable to detect identifiers. For example, the communication components 740 may include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code, UCC RSS-2D bar code, and other optical codes), or acoustic detection components (e.g., microphones to identify tagged audio signals). In addition, a variety of information may be derived via the communication components 740, such as, location via Internet Protocol (IP) geo-location, location via Wi-Fi® signal triangulation, location via detecting a NFC beacon signal that may indicate a particular location, and so forth.

Glossary

"CARRIER SIGNAL" in this context refers to any intangible medium that is capable of storing, encoding, or carrying instructions for execution by the machine, and includes digital or analog communications signals or other intangible medium to facilitate communication of such instructions. Instructions may be transmitted or received over the network using a transmission medium via a network interface device and using any one of a number of well-known transfer protocols.

"CLIENT DEVICE" in this context refers to any machine that interfaces to a communications network to obtain resources from one or more server systems or other client devices. A client device may be, but is not limited to, a mobile phone, desktop computer, laptop, portable digital assistants (PDAs), smart phones, tablets, ultra books, netbooks, laptops, multi-processor systems, microprocessor-based or programmable consumer electronics, game consoles, set-top boxes, or any other communication device that a user may use to access a network.

"COMMUNICATIONS NETWORK" in this context refers to one or more portions of a network that may be an ad hoc network, an intranet, an extranet, a virtual private network (VPN), a local area network (LAN), a wireless LAN (WLAN), a wide area network (WAN), a wireless WAN (WWAN), a metropolitan area network (MAN), the Internet, a portion of the Internet, a portion of the Public Switched Telephone Network (PSTN), a plain old telephone service (POTS) network, a cellular telephone network, a wireless network, a Wi-Fi® network, another type of network, or a combination of two or more such networks. For example, a network or a portion of a network may include a wireless or cellular network and the coupling may be a Code Division Multiple Access (CDMA) connection, a Global System for Mobile communications (GSM) connection, or other type of cellular or wireless coupling. In this example, the coupling may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS), High Speed Packet Access (HSPA), Worldwide Interoperability for Microwave Access (WiMAX), Long Term Evolution (LTE) standard, others defined by various standard setting organizations, other long range protocols, or other data transfer technology.

"MACHINE-READABLE MEDIUM" in this context refers to a component, device or other tangible media able to store instructions and data temporarily or permanently and may include, but is not limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions. The term "machine-readable medium" shall also be taken to include any medium, or combination of multiple media, that is capable of storing instructions (e.g., code) for execution by a machine, such that the instructions, when executed by one or more processors of the machine, cause the machine to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

"COMPONENT" in this context refers to a device, physical entity or logic having boundaries defined by function or subroutine calls, branch points, application program interfaces (APIs), or other technologies that provide for the partitioning or modularization of particular processing or control functions. Components may be combined via their interfaces with other components to carry out a machine process. A component may be a packaged functional hardware unit designed for use with other components and a part of a program that usually performs a particular function of related functions. Components may constitute either software components (e.g., code embodied on a machine-readable medium) or hardware components. A "hardware component" is a tangible unit capable of performing certain operations and may be configured or arranged in a certain physical manner. In various example embodiments, one or more computer systems (e.g., a standalone computer system, a client computer system, or a server computer system) or one or more hardware components of a computer system (e.g., a processor or a group of processors) may be configured by software (e.g., an application or application portion) as a hardware component that operates to perform certain operations as described herein. A hardware component may also be implemented mechanically, electronically, or any suitable combination thereof. For example, a hardware component may include dedicated circuitry or logic that is permanently configured to perform certain operations. A hardware component may be a special-purpose processor, such as a Field-Programmable Gate Array (FPGA) or an Application Specific Integrated Circuit (ASIC). A hardware component may also include programmable logic or circuitry that is temporarily configured by software to perform certain operations. For example, a hardware component may include software executed by a general-purpose processor or other programmable processor. Once configured by such software, hardware components become specific machines (or specific components of a machine) uniquely tailored to perform the configured functions and are no longer general-purpose processors. It will be appreciated that the decision to implement a hardware component mechanically, in dedicated and permanently configured circuitry, or in temporarily configured circuitry (e.g., configured by software) may be driven by cost and time considerations. Accordingly, the phrase "hardware component" (or "hardware-implemented component") should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware components are temporarily configured (e.g., programmed), each of the hardware components need not be configured or instantiated at any one instance in time. For example, where a hardware component comprises a general-purpose processor configured by software to become a special-purpose processor, the general-purpose processor may be configured as respectively different special-purpose processors (e.g., comprising different hardware components) at different times. Software accordingly configures a particular processor or processors, for example, to constitute a particular hardware component at one instance of time and to constitute a different hardware component at a different instance of time. Hardware components can provide information to, and receive information from, other hardware components. Accordingly, the described hardware components may be regarded as being communicatively coupled. Where multiple hardware components exist contemporaneously, communications may be achieved through signal transmission (e.g., over appropriate circuits and buses) between or among two or more of the hardware components. In embodiments in which multiple hardware components are configured or instantiated at different times, communications between such hardware components may be achieved, for example, through the storage and retrieval of information in memory structures to which the multiple hardware components have access. For example, one hardware component may perform an operation and store the output of that operation in a memory device to which it is communicatively coupled. A further hardware component may then, at a later time, access the memory device to retrieve and process the stored output. Hardware components may also initiate communications with input or output devices, and can operate on a resource (e.g., a collection of information). The various operations of example methods described herein may be performed, at least partially, by one or more processors that are temporarily configured (e.g., by software) or permanently configured to perform the relevant operations. Whether temporarily or permanently configured, such processors may constitute processor-implemented components that operate to perform one or more operations or functions described herein. As used herein, "processor-implemented component" refers to a hardware component implemented using one or more processors. Similarly, the methods described herein may be at least partially processor-implemented, with a particular processor or processors being an example of hardware. For example, at least some of the operations of a method may be performed by one or more processors or processor-implemented components. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)). The performance of certain of the operations may be distributed among the processors, not only residing within a single machine, but deployed across a number of machines. In some example embodiments, the processors or processor-implemented components may be located in a single geographic location (e.g., within a home environment, an office environment, or a server farm). In other example embodiments, the processors or processor-implemented components may be distributed across a number of geographic locations.

"PROCESSOR" in this context refers to any circuit or virtual circuit (a physical circuit emulated by logic executing on an actual processor) that manipulates data values according to control signals (e.g., "commands", "op codes", "machine code", etc.) and which produces corresponding output signals that are applied to operate a machine. A processor may, for example, be a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuit (ASIC), a Radio-Frequency Integrated Circuit (RFIC) or any combination thereof. A processor may further be a multi-core processor having two or more independent processors (sometimes referred to as "cores") that may execute instructions contemporaneously.

What is claimed is:
1. A method comprising:
causing a sensor device to sample an air quality associated with a location at a predefined sampling interval, the sensor device including a first sensor device;
determining, at the first sensor device, that a value corresponding with the air quality sampled by the first sensor device transgresses a threshold value;
causing the first sensor device to transmit an alert to a server system responsive to the determining that the value corresponding with the air quality transgresses a threshold value;
activating a second sensor device from among a plurality of sensor devices based on the alert; and
causing the server system to present a notification within a graphical user interface (GUI) that includes a map image at a client device based on the alert, the notification including at least a display of an icon at position that corresponds with the location within the map image, and sensor data generated by the first sensor device and the second sensor device.

2. The method of claim 1, wherein the sampling interval is a first sampling interval, and the method further comprises:
causing the first sensor device to sample the air quality associated with the location at a second sampling interval responsive to the determining that the value corresponding with the air quality sampled by the sensor device transgresses the threshold value.

3. The method of claim 2, wherein the second sampling interval is higher than the first sampling interval.

4. The method of claim 1, wherein the notification further comprises a presentation of one or more identifiers that identify the first sensor device and the second sensor device.

5. The method of claim 1, further comprising:
receiving an input that selects the icon from within the GUI presented at the client device; and
causing display of a menu element that displays attributes associated with the at least the first sensor device responsive to the input that selects the icon.

6. The method of claim 1, wherein the identifier includes a location identifier that identifies the location, and sensor identifiers that identify the first sensor device and the second sensor device.

7. The method of claim 1, wherein the causing the first sensor device to sample the air quality associated with the location at the predefined sampling interval further comprises:
causing the first sensor device to transmit the value corresponding with the air quality to the server at the predefined sampling interval.

8. A system comprising:
a memory; and
at least one hardware processor to perform operations comprising:

causing a sensor device to sample an air quality associated with a location at a predefined sampling interval, the sensor device including a first sensor device;

determining, at the first sensor device, that a value corresponding with the air quality sampled by the first sensor device transgresses a threshold value;

causing the first sensor device to transmit an alert to a server system responsive to the determining that the value corresponding with the air quality transgresses a threshold value;

activating a second sensor device from among a plurality of sensor devices based on the alert; and causing the server system to present a notification within a graphical user interface (GUI) that includes a map image at a client device based on the alert, the notification including at least a display of an icon at position that corresponds with the location within the map image, and sensor data generated by the first sensor device and the second sensor device.

9. The system of claim 8, wherein the sampling interval is a first sampling interval, and the operations further comprise:

causing the sensor device to sample the air quality associated with the location at a second sampling interval responsive to the determining that the value corresponding with the air quality sampled by the first sensor device transgresses the threshold value.

10. The system of claim 9, wherein the second sampling interval is higher than the first sampling interval.

11. The system of claim 8, wherein the notification further comprises a presentation of one or more identifiers that identify the first sensor device and the second sensor device.

12. The system of claim 8, further comprising:

receiving an input that selects the icon from within the GUI presented at the client device; and causing display of a menu element that displays attributes associated with the at least the first sensor device responsive to the input that selects the icon.

13. The system of claim 8, wherein the identifier includes a location identifier that identifies the location, and sensor identifiers that identify the first sensor device and the second sensor device.

14. The system of claim 8, wherein the causing the first sensor device to sample the air quality associated with the location at the predefined sampling interval further comprises:

causing the first sensor device to transmit the value corresponding with the air quality to the server at the predefined sampling interval.

15. A non-transitory machine-readable storage medium comprising instructions that, when executed by one or more processors of a machine, cause the machine to perform operations comprising:

causing a sensor device to sample an air quality associated with a location at a predefined sampling interval, the sensor device including a first sensor device;

determining, at the first sensor device, that a value corresponding with the air quality sampled by the first sensor device transgresses a threshold value;

causing the first sensor device to transmit an alert to a server system responsive to the determining that the value corresponding with the air quality transgresses a threshold value;

activating a second sensor device from among a plurality of sensor devices based on the alert; and causing the server system to present a notification within a graphical user interface (GUI) that includes a map image at a client device based on the alert, the notification including at least a display of an icon at position that corresponds with the location within the map image, and sensor data generated by the first sensor device and the second sensor device.

16. The non-transitory machine-readable storage medium of claim 15, wherein the sampling interval is a first sampling interval, and the operations further comprise:

causing the first sensor device to sample the air quality associated with the location at a second sampling interval responsive to the determining that the value corresponding with the air quality sampled by the first sensor device transgresses the threshold value.

17. The non-transitory machine-readable storage medium of claim 15, wherein the second sampling interval is higher than the first sampling interval.

18. The non-transitory machine-readable storage medium of claim 15, wherein the notification further comprises a presentation of one or more identifiers that identify the first sensor device and the second sensor device.

19. The non-transitory machine-readable storage medium of claim 15, further comprising:

receiving an input that selects the icon from within the GUI presented at the client device; and causing display of a menu element that displays attributes associated with the at least the first sensor device responsive to the input that selects the icon.

20. The non-transitory machine-readable storage medium of claim 15, wherein the identifier includes a location identifier that identifies the location, and sensor identifiers that identify the first sensor device and the second sensor devices.

\* \* \* \* \*